US011760993B2

(12) United States Patent
Chin et al.

(10) Patent No.: US 11,760,993 B2
(45) Date of Patent: Sep. 19, 2023

(54) HIGH EFFICIENT INDEXING METHOD FOR GENOME ASSEMBLY

(71) Applicant: OmniBioComputing LLC, Santa Clara, CA (US)

(72) Inventors: Chen-Shan Chin, San Leandro, CA (US); Wangchang Hou, San Jose, CA (US); Asif Khalak, Belmont, CA (US)

(73) Assignee: OmniBioComputing LLC, Santa Clara, CA (US)

( * ) Notice: Subject to any disclaimer, the term of this patent is extended or adjusted under 35 U.S.C. 154(b) by 456 days.

(21) Appl. No.: 16/878,051

(22) Filed: May 19, 2020

(65) Prior Publication Data

US 2020/0370038 A1  Nov. 26, 2020

Related U.S. Application Data

(60) Provisional application No. 62/850,142, filed on May 20, 2019.

(51) Int. Cl.
*C12N 15/10* (2006.01)
*C12Q 1/6874* (2018.01)

(52) U.S. Cl.
CPC ....... *C12N 15/1027* (2013.01); *C12Q 1/6874* (2013.01)

(58) Field of Classification Search
CPC ... C12N 15/1027; C12Q 1/6874; G16B 30/20
See application file for complete search history.

(56) References Cited

U.S. PATENT DOCUMENTS

2015/0211054 A1\* 7/2015 Kostem .................. G16B 20/00
702/19

OTHER PUBLICATIONS

Mitchell R. Vollger et al, Improved assembly and variant detection of a haploid human genome using single-molecule, high-fidelity long reads, bioRxiv preprint first posted online May 10, 2019; doi: http://dx.doi.org/10.1101/635037 (27 pages).
Ameur A., et al., "De Novo Assembly of Two Swedish Genomes Reveals Missing Segments from the Human GRCh38 Reference and Improves Variant Calling of Population-Scale Sequencing Data," Genes, Oct. 9, 2018, vol. 9 (10), 16 pages.
Berlin K., et al., "Assembling Large Genomes with Single-molecule Sequencing and Locality-sensitive Hashing," Aug. 2014, 35 pages.
(Continued)

*Primary Examiner* — Kyoung Lee
(74) *Attorney, Agent, or Firm* — Fish IP Law, LLP

(57) ABSTRACT

Methods, systems, and devices are contemplated for assembling a genome from duplicate segments of the genome. Sequences with a first level of common neighboring base pairs are identified and organized into first level groups. Groups are then identified from the first level groups that have a second level of common neighboring base pairs and organized into a number of second level groups. A third level of groups can further be organized in some embodiments. Typically the second level groups are assembled into spans having contiguous base pair sequences, which are then assembled into the broader genome sequence. The inventive subject matter is preferably used for whole genome sequencing.

19 Claims, 14 Drawing Sheets

(56) References Cited

OTHER PUBLICATIONS

Berlin K., et al., "Assembling Large Genomes with Single-molecule Sequencing and Locality-sensitive Hashing," Nature Biotechnology, Jun. 2015, vol. 33 (6), 12 pages.
Chaisson M.J.P., et al., "Genetic Variation and the de novo Assembly of Human Genomes," Nature Reviews Genetics, Nov. 2015, vol. 16 (11), 31 pages.
Chaisson M.J.P., et al., "Resolving the Complexity of the Human Genome using Single-molecule Sequencing," Nature, Jan. 2015, vol. 517 (7536), 17 pages.
Chin C.S., et al., "Nonhybrid, Finished Microbial Genome Assemblies from Long-read SMRT Sequencing Data," Nature Methods, Jun. 2013, vol. 10 (6), 9 pages.
Chin C.S., et al., "Phased Diploid Genome Assembly with Single Molecule Real-Time Sequencing," Nature Methods, Dec. 2016, vol. 13(12), 18 pages.
Denny J.C., et al., "PheWAS: Demonstrating the Feasibility of a Phenome-wide Scan to Discover Gene-disease Associations," Bioinformatics, 2010, vol. 26 (9), pp. 1205-1210.
Gordon D., et al., "Long-read Sequence Assembly of the Gorilla Genome," Science, Apr. 2016, vol. 352 (6281), 21 pages.
Hood L., et al., "The Human Genome Project: Big Science Transforms Biology and Medicine," Genome Medicine, Sep. 2013, vol. 5 (9), 8 pages.
Jain M., et al., "Nanopore Sequencing and Assembly of a Human Genome with Ultra-long Reads," Nature Biotechnology, Jan. 2018, vol. 36, 16 pages.
Kececioglu J.D., et al., "Combinatorial Algorithms for DNA Sequence Assembly," Algorithmica, 1995, vol. 13, pp. 7-51.
Kolmogorov M., et al., "Assembly of Long Error-Prone Reads Using Repeat Graphs," Nature biotechnology, 2019, vol. 37, 29 pages.
Koren S., et al., "De novo Assembly of Haplotype-resolved Genomes with Trio Binning," Nature Biotechnology, Apr. 2019, 25 pages.
Lander E.S., "Initial Impact of the Sequencing of the Human Genome," Nature, 2011, vol. 470, 44 pages.

Li H., "Minimap and Miniasm: Fast Mapping and de novo Assembly for Noisy Long Sequences," Bioinformatics, Jul. 2016, vol. 32 (14), pp. 2103-2110.
Motahari A.S., et al., "Information Theory of DNA Shotgun Sequencing," IEEE Transactions on Information Theory, Oct. 2013, vol. 59 (10), pp. 6273-6289.
Myers E.W., "An O(ND) Difference Algorithm and Its Variations," Algorithmica, 1986, vol. 1, pp. 251-266.
Myers E.W., "The Fragment Assembly String Graph," Bioinformatics, 2005, vol. 21 (2), pp. ii79-ii85.
Myers G., "Efficient Local Alignment Discover amongst Noisy Long Reads," International Workshop on Algorithms in Bioinformatics, 2014, 2 pages.
Ruan J., et al., "Fast and accurate long-read assembly with wtdbg2," Nature Methods, Jan. 2019, vol. 17, 7 pages.
Schneider V.A., "Evaluation of GRCh38 and de novo Haploid Genome Assemblies Demonstrates the Enduring Quality of the Reference Assembly," Genome Research, May 2017, vol. 27 (5), pp. 849-864.
Seo J.S., "De novo Assembly and Phasing of a Korean Human Genome," Nature, Oct. 2016, vol. 538, 18 pages.
Simao F.A., et al., "BUSCO: Assessing Genome Assembly and Annotation Completeness with Single-copy Orthologs," Bioinformatics, Oct. 2015, vol. 31 (19), pp. 3210-3212.
Visscher P.M., et al., "10 Years of GWAS Discovery: Biology, Function, and Translation," The American Journal of Human Genetics, Jul. 6, 2017, vol. 101 (1), pp. 5-22.
Vollger M.R., et al., "Improved Assembly and Variant Detection of a Haploid Human Genome using Single-molecule, High-fidelity Long Reads," Aug. 2019, 49 pages.
Welter D., et al., "The NHGRI GWAS Catalog, a curated resource of SNP-trait associations," Nucleic Acids Research, 2014, vol. 42, pp. D1001-D1006.
Wenger A.M., et al., "Highly-accurate Long-read Sequencing Improves Variant Detection and Assembly of a Human Genome," 2019, Supplementary material, pp. S-1 to S-23.
Wenger A.M., et al., "Highly-accurate Long-read Sequencing Improves Variant Detection and Assembly of a Human Genome," Nature Biotechnology, Jan. 2019, vol. 37, 28 pages.

* cited by examiner

SHIMMER index:
hashmap F: $(m_1, m_2) \rightarrow \{r_1, r_2, ...\}$
hashmap F: $(m_2, m_3) \rightarrow \{r_1, r_2, r_3, ...\}$
...

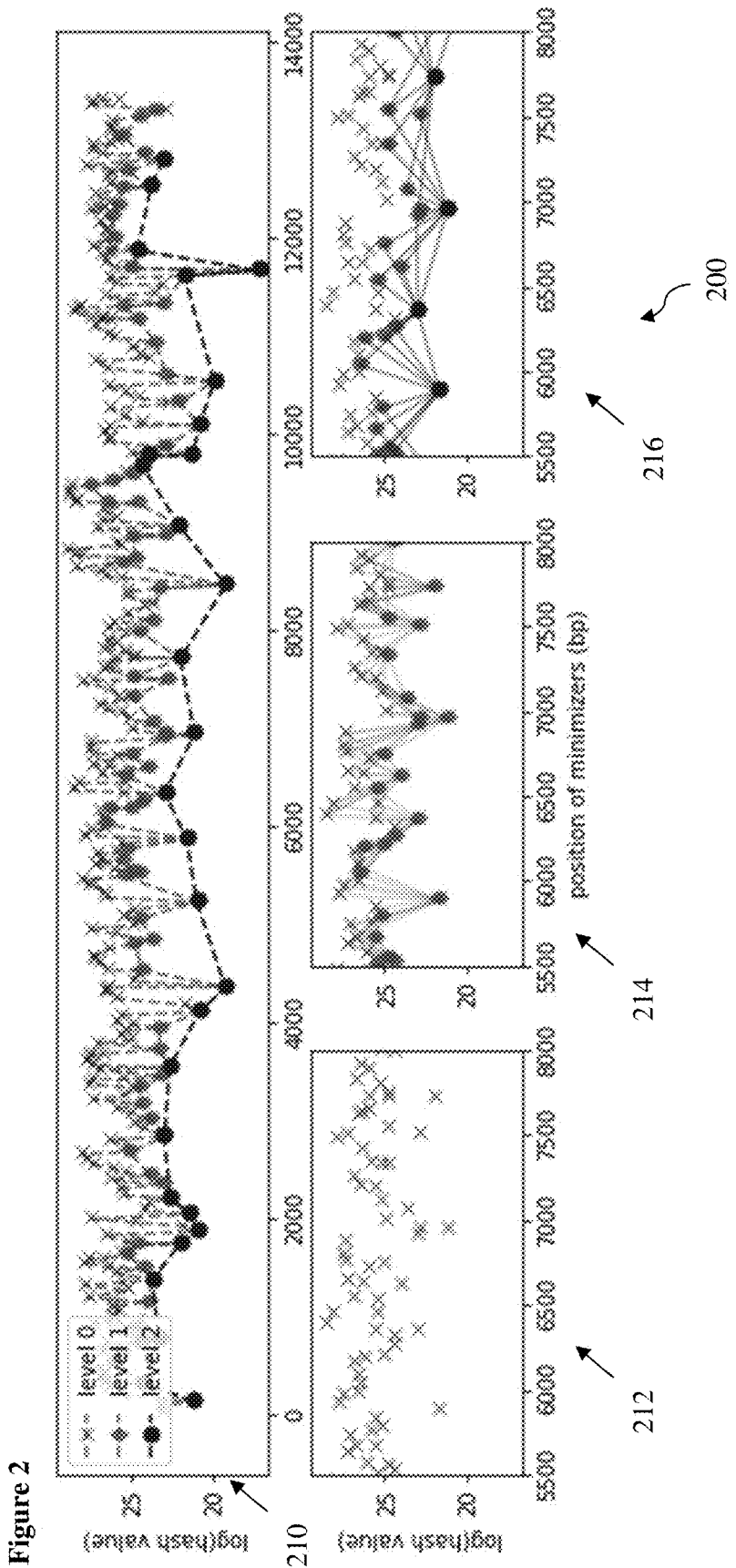

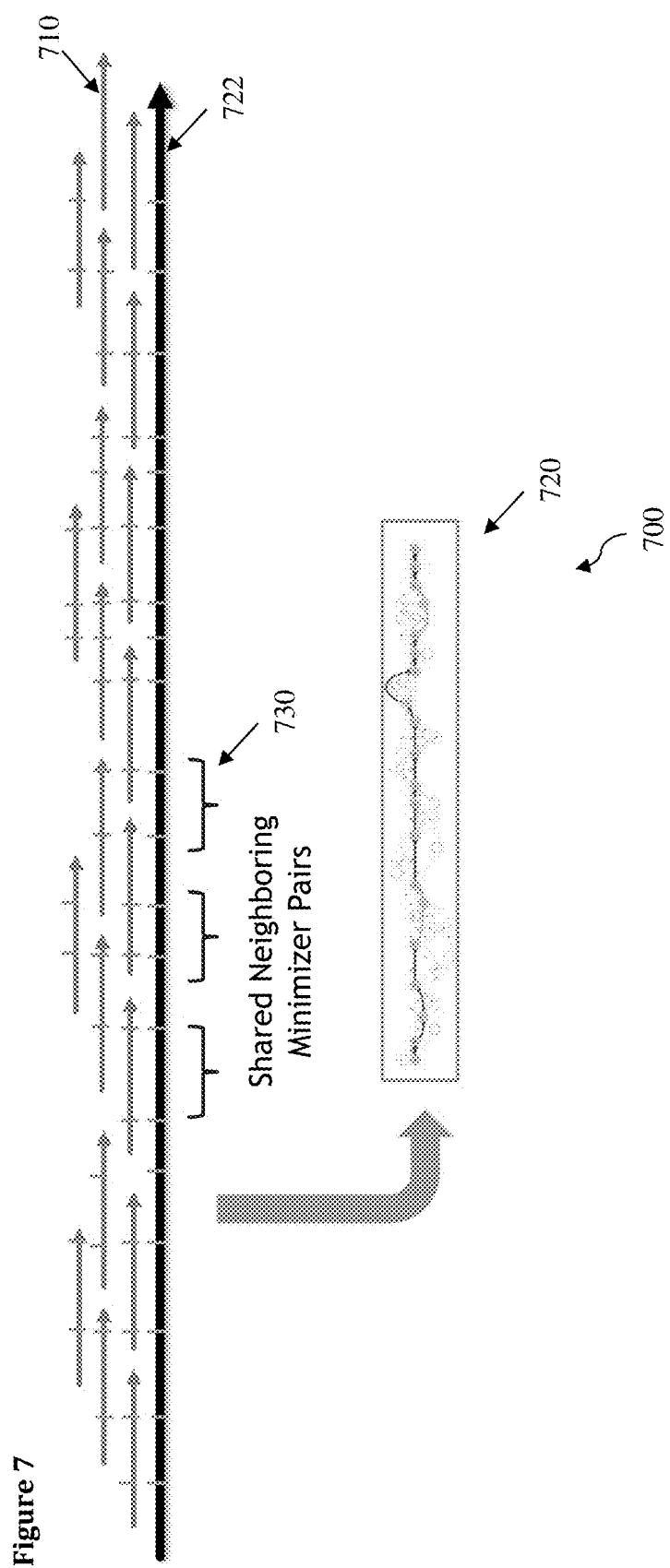

| Disk Usage | | | | | | |
|---|---|---|---|---|---|---|
| Genome | parameters | read length | # reads | seqdb | L0 index | L2 or L1 index |
| hg002 | r=6, l=2 | 13478.3 | 6610240 | 89.1 Gb | 44.7 Gb | 4.46 Gb |
| hg002 | r=4, l=2 | 13478.3 | 6610240 | 89.1 Gb | 44.7 Gb | 9.51 Gb |
| hg002 | r=18, l=1 | 13478.3 | 6610240 | 89.1 Gb | 44.7Gb | 4.84 Gb |
| hg002 | r=36, l=1 | 13478.3 | 6610240 | 89.1 Gb | 44.7Gb | 2.38 Gb |
| hg002 (Sequel II) | r=6, l=2 | 11301.3 | 3895357 | 44.2 Gb | 24.2 Gb | 5.13 Gb |
| chm13 | r=4, l=2 | 10960.1 | 6902752 | 75.7 Gb | 38.6 Gb | 8.20 Gb |
| chm13 | r=3, l=2 | 10960.1 | 6902752 | 75.7 Gb | 38.6 Gb | 13.08 Gb |
| pgp-1 | r=4, l=2 | 12598.2 | 5701675 | 71.8 Gb | 37.1 Gb | 7.89 Gb |
| pgp-1 | r=3, l=2 | 12598.2 | 5701675 | 71.8 Gb | 37.1 Gb | 12.58Gb |
| NA12878 | r=3, l=2 | 9963.2 | 9082038 | 90.5 Gb | 45.3 Gb | 15.34 Gb |

Figure 9

| Run Time (CPU Hours) | | | | | | | | |
|---|---|---|---|---|---|---|---|---|
| Genome | parameters | seqdb building | indexing | overlapping | overlaps to contigs | consensus | total | instance type |
| hg002 | r=6, l=2 | 0.073 | 0.493 | 6.687 | 0.716 | 8.290 | 16.259 | m5d.metal |
| hg002 | r=4, l=2 | 0.080 | 0.511 | 11.880 | 0.800 | 7.325 | 20.596 | m5d.metal |
| hg002 | r=18, l=1 | 0.081 | 0.491 | 7.767 | 0.743 | 6.736 | 15.818 | m5d.metal |
| hg002 | r=36, l=1 | 0.075 | 0.494 | 3.646 | 0.641 | 7.023 | 11.879 | m5d.metal |
| hg002 (Sequel II) | r=6, l=2 | 0.027 | 0.256 | 4.139 | 0.463 | 4.397 | 9.282 | m5d.metal |
| chm13 | r=4, l=2 | 0.067 | 0.443 | 6.822 | 0.630 | 7.453 | 15.415 | r5d.12xlarge |
| chm13 | r=3, l=2 | 0.061 | 0.452 | 8.897 | 0.682 | 6.297 | 16.389 | r5d.12xlarge |
| pgp-1 | r=4, l=2 | 0.045 | 0.405 | 8.151 | 0.323 | 6.610 | 15.534 | m5d.metal |
| pgp-1 | r=3, l=2 | 0.047 | 0.403 | 10.846 | 0.365 | 7.145 | 18.806 | m5d.metal |
| NA12878 | r=3, l=2 | 0.075 | 0.519 | 13.785 | 1.911 | 9.038 | 25.328 | m5d.metal |

Figure 10

Assembly Statistics Summary

| Genome | parameters | Total | N50 | max | # seq |
|---|---|---|---|---|---|
| hg002 | r=6, l=2 | 2,896,918,528 | 27,848,727 | 108,387,980 | 2,398 |
| hg002 | r=4, l=2 | 2,906,581,718 | 33,364,927 | 108,396,082 | 2,438 |
| hg002 | r=18, l=1 | 2,897,055,690 | 26,459,768 | 102,052,462 | 2,384 |
| hg002 | r=36, l=1 | 2,894,701,861 | 6,746,698 | 32,267,778 | 3,194 |
| hg002 (Sequel II) | r=6, l=2 | 2,872,604,008 | 21,936,975 | 109,829,231 | 2,022 |
| chm13 | r=4, l=2 | 2,839,105,926 | 29,260,433 | 102,007,116 | 978 |
| chm13 | r=3, l=2 | 2,838,663,153 | 33,307,555 | 95,435,791 | 844 |
| pgp-1 | r=4, l=2 | 2,929,632,487 | 27,316,706 | 109,849,654 | 2,816 |
| pgp-1 | r=3, l=2 | 2,941,861,553 | 28,222,972 | 90,594,607 | 2,948 |
| NA12878 | r=3, l=2 | 2,880,983,308 | 25,483,577 | 109,846,404 | 3,061 |

Figure 11

| | parameters | Complete (%) | Complete Single Copy (%) | Complete and duplicated (%) | Fragmented (%) | Missing (%) | Total BUSCO groups |
|---|---|---|---|---|---|---|---|
| HG002 | r=3, l=2 | 95.0 | 93.7 | 1.3 | 2.3 | 2.7 | 2586 |
| CHM13 | r=3, l=2 | 94.0 | 92.8 | 1.2 | 2.7 | 3.3 | 2586 |
| NA12878 | r=3, l=2 | 95.2 | 93.9 | 1.3 | 2.3 | 2.5 | 2586 |

Figure 12

HIGH EFFICIENT INDEXING METHOD FOR GENOME ASSEMBLY

This application claims priority to U.S. provisional application No. 62/850,142, filed May 20, 2019, the disclosure of which is incorporated herein by reference.

FIELD OF THE INVENTION

The field of the invention is in the field of determining nucleotide sequences from biological samples and DNA sequencing data.

BACKGROUND

Whole genome shotgun sequencing (WGS) has become the standard for determining the chromosomal sequences for human and other organisms. Constructing genomes from WGS is one of the cornerstones for modern day biotech industry. The current method for generating de novo assembly requires significant amount of computational resources.

The WGS typically generates DNA reads from a high number of DNA fragments from a genome. For example, if one sequences a human genome (3 billion bases) with DNA fragment lengths of 10 kb, there will be 300,000 such fragments. Due to the random sampling nature for the whole genome shotgun sequencing protocol, a high number of redundancies is typically needed for successful de novo assembly. Typically, 30-fold or higher redundancy will be needed for successfully reconstructing long contiguous sequences (contigs) from the chromosomes. For 30× human genomes, there will be 9,000,000 reads.

Pioneered by Gene Myers, et. al, (U.S. Pat. No. 6,714,874B1), the "overlap-layout-consensus" paradigm remains one of the most used methods for de novo assembly of genomes. The "overlap" step includes testing if any two fragments in the data set may come from the same region of a genome. For the 30× human genome example, it means testing all pairs of the 9,000,000 reads. Namely, a computational system to determine the overlap between reads will need $9,000,000*9,000,000=8.1*10^{13}$ tests for the de novo assembly of a human genome.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Most methods used for genome assembly includes such read-to-read comparisons. Even with the advance of computation hardware and software, it typically still takes a couple thousand of CPU hours to assemble a human genome. See, e.g., Vollger, et al., "Improved assembly and variant detection of a haploid human genome using single-molecule, high-fidelity long reads," bioRxiv, 2019. Many assembly methods focus on reducing the computation time for each of the comparative tests. The number of comparisons performed is still proportional to the square of the number of fragments.

Indexing DNA sequencing reads is also widely used for various DNA sequence processing. For example, Burrow-Wheeler Transformation (BWT) with FM-index (Paolo Ferragina and Giovanni Manzini (2005). "Indexing Compressed Text". Journal of the ACM, 52, 4 (July 2005). p. 553) are adapted for mapping reads to a reference sequence. The other common indexing methods for fast sequence search and mapping is "minimizer" (Roberts, Michael, Wayne Hayes, Brian R. Hunt, Stephen M. Mount, and James A. Yorke. "Reducing storage requirements for biological sequence comparison." Bioinformatics 20, no. 18 (2004): 3363-3369.) In contrast to the BWT and FM-index, minimizer is more effective for indexing long DNA fragment for more effective search.

A minimizer is a k-mer (k consecutive DNA bases in DNA sequencing reads) that is one of a curated list of k-mers such that any significant overlapping exact match between reads is composed of w consecutive k-mers contained in the list. Such lists, which characterize significant matches will generally be far smaller in size than the reads themselves. The process of generating minimizers is akin to database indexing.

Long repetitive sequences in a genome usually pose computational challenges for the overlapping step. For example, if a sequence is repeated M times and the sequencing depth is N times of the genome size, there are potentially $(MN)^2$ reads that are mostly identical to each other. The extra $M^2$ factor can significantly increase the computation time and storage requirement for the read overlapping step. Various heuristics are used to reduce this extra computation burden (Chin, Chen-Shan, Paul Peluso, Fritz J. Sedlazeck, Maria Nattestad, Gregory T. Concepcion, Alicia Clum, Christopher Dunn et al. "Phased diploid genome assembly with single-molecule real-time sequencing." Nature methods 13, no. 12 (2016): 1050.).

Thus, there is still a need for improved methods of sequencing genomes, such as improved computational methods for assembling whole genome from millions of short reads.

SUMMARY OF THE INVENTION

Methods, systems, and devices are contemplated for assembling a genetic sequence (e.g., whole genome, partial, etc.) from a number of at least partially duplicate segments of the genetic sequence. Sequences (at least two, preferably thousands, tens of thousands, or hundreds of thousands, some, most, all, etc.) with a first level of minimizers (e.g., common neighboring base pairs, etc.) are identified and organized into first level groups (tier 1). In some embodiments, the first level groups are assembled into spans of contiguous base pair sequences, which are then assembled into the broader genetic sequence. However, it is also contemplated that further groups are identified from the first level groups that have a second level of minimizers (e.g., common neighboring base pairs) (at least some, most, or all) and organized into a plurality of second level groups (tier 2). The second level groups (at least some, most, or all or substantially all) are then assembled into spans having contiguous base pair sequences.

Viewed from another perspective, the second level of minimizers (e.g., shared neighboring base pairs) are used to arrange segments of each second level group into a contiguous sequence of base pairs. The contiguous sequences are then assembled into the broader genetic sequence. The inventive subject matter is preferably used for whole genome sequencing, though partial genome sequencing is also contemplated.

The sequences are typically more than ten base pairs long, but can be as few as five base pairs or more than one hundred or one thousand base pairs. The first level of minimizers (e.g., common neighboring base pairs) are typically identified in a read window of at least forty base pairs, or more than eighty or one hundred twenty base pairs. In some embodiments the first level of minimizers (e.g., common neighboring base pairs) are separated by at least fifty base pairs, or more than one hundred base pairs. The second level of minimizers (e.g., common neighboring base pairs) are typically separated by at least three hundred base pairs, or more than five hundred or six hundred base pairs.

Further methods, systems, and devices are contemplated for assembling a genetic sequence (e.g., genome, partial genome, etc.) from a number of at least partially duplicate segments of the genetic sequence. Sequences (at least two, preferably thousands, tens of thousands, or hundreds of thousands, etc.) with a first level of common neighboring base pairs are identified and organized into a number of first level groups (tier 1). Groups are then identified from the first level groups that have a second level common neighboring base pair and are organized into a number of second level groups (tier 2). Groups are then identified from the second level groups with a third level common neighboring base pair, and organized into a number of third level groups (tier 3). Each of the third level groups is then assembled into spans having contiguous base pair sequences, and the spans are assembled to construct the broader genetic sequence. The third level common neighboring base pairs of the third level groups are typically separated by at least six hundred base pairs, or more than eight hundred or one thousand base pairs.

Systems, methods, and devices are further contemplated for building a data structure from at least partially duplicate segments of a genetic sequence. Primary groups of segments are assembled, wherein each primary group (in some embodiments mostly or exclusively) includes segments with a first order of common neighboring base pairs. The primary groups (some or most, preferably all) are then assembled into secondary groups, wherein each primary group in a secondary group includes a segment with a second order of common neighboring base pairs. In some embodiments, the of secondary groups are further assembled into a plurality of tertiary groups, wherein each secondary group in a tertiary group includes a segment with a third order of common neighboring base pairs.

Systems, methods, and devices are further contemplated for assembling a data sequence from a number of at least partially duplicate segments of the data sequence. Data sequences (at least two, preferably thousands, tens of thousands, hundreds of thousands or more, etc.) with a first level of common neighboring data elements are identified and organized into a number of first level groups (tier 1). Groups from the first level groups are identified that have a second level common neighboring data element and are organized into a plurality of second level groups (tier 2). The second level groups (at least some, preferably all or substantially all) are then assembled into spans with a contiguous sequence of data elements. The spans (some, most, or all) are then assembled into the broader data sequence. Preferably the entire data sequence is assembled, though assembly of a partial data sequence is also contemplated.

The data sequences typically include more than ten consecutive data elements, but can include as few as five or more than one hundred or one thousand consecutive data elements. The first level of common neighboring data elements are typically identified in a read window of at least forty data elements, or more than twenty, eighty, one hundred twenty, two hundred, or five hundred data elements. In some embodiments the first level of common neighboring data elements are separated by at least fifty data elements, or more than twenty, one hundred, five hundred, or one thousand data elements. The second level of common neighboring data elements are typically separated by at least three hundred data elements, or more than one hundred, five hundred, one thousand, or five thousand data elements.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 2 depicts hashmaps of indexes of the inventive subject matter.

FIG. 7 depicts a pictorial of workflows of the inventive subject matter.

FIG. 9 depicts data using systems and methods of the inventive subject matter.

FIG. 10 depicts more data using systems and methods of the inventive subject matter.

FIG. 11 depicts yet more data using systems and methods of the inventive subject matter.

FIG. 12 depicts even more data using systems and methods of the inventive subject matter.

DETAILED DESCRIPTION

Figure 1A:
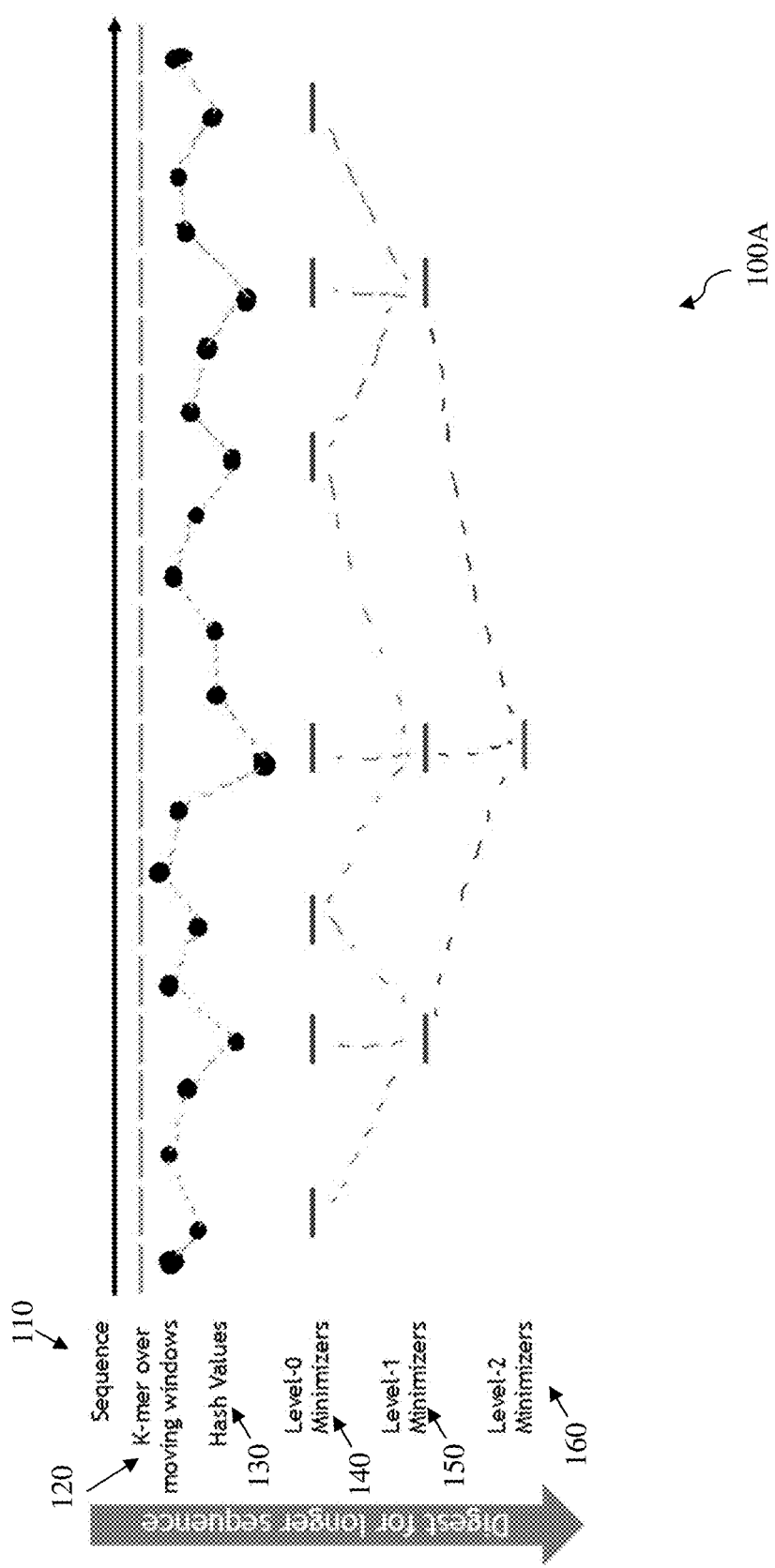
FIG. 1A depicts a pictorial of sparse & hierarchical minimizer ("SHIMMER") indexing of the inventive subject matter.

The inventive subject matter includes a new indexing method for DNA sequencing reads. The new indexing method significantly reduces the computation resource required for determining DNA sequences of genomes, for example via whole genome shotgun sequencing methods. Among other improvements, the inventive subject matter eliminates quadratic comparison steps of the prior art. Systems and methods of the inventive subject matter index reads to group the reads that are likely from the same regions of a genome together before any direct read-to-read comparison or alignment.

The inventive subject matter presents a method of indexing DNA sequencing reads with sparse hierarchical minimizers ("SHIMMER") to enable fast genome assembly computation. Instead of testing all reads against each other in the read dataset, DNA sequencing reads that have a high likelihood of overlapping with each other are grouped in the SHIMMER index. By eliminating quadratic read-to-read overlapping tests previously used for genome assembly, the invention makes the assembly process orders of magnitude faster and uses smaller disk storage for indices, enabling hardware to perform new processes and functions that were previously unattainable.

Viewed from another perspective, the inventive subject matter provides apparatus, systems and methods in which a computation device or devices can build the SHIMMER index structure storing in computer memory and disk. The computing device or devices can utilize the index structure for generating genome assembly and consensus sequences from DNA fragment reads stored in RAM or disk.

Starting from DNA sequencing reads, the minimizers are identified along the reads as the level-0 minimizers. The level-0 minimizers identified with a moving window size w is a concise digest of the sequence around the minimizers up the length w. We further reduce the number of minimizers be finding higher level of minimizers from the lower level one so the minimizers in the higher level represents bigger windows approximately r*w, where r is the reduction factor. For example, if w is used for the level-0 minimizers and we identify level-1minimizer using r=3. The level-1 minimizers can be seen as a digest of the underlying sequences of window size 3 w. Since each higher-level minimizers represent larger windows, we will need smaller number of minimizers for indexing DNA reads. The sparse minimizers can be also constructed directly using larger w=60, 80, 100, 200, 500, 1000 directly in the level-0 minimizer generation.

In order to increase the specificity of predicting overlapped DNA reads, methods of the inventive subject matter include the SHIMMER index using neighboring 2,3,4,5,6,7,8,9,10,11, or 12 minimizers as the keys of a HashMap. The values of the HashMap corresponding to each key are the list of DNA reads which are likely to overlap with each other as they share the same neighboring sparse minimizers.

Using neighboring minimizers to group reads that likely overlaps with each other significantly reduces the computation resource requirement for detecting all pairs of overlapped reads, as a pair of reads that do not share the neighboring minimizers are not likely to overlap. In our methods, the reads that do not overlap with other will have different keys, thus, an explicit test to confirm such reads are not overlapped with each other is unnecessary.

Only reads that are binned together are compared to each other to confirm proper overlapping. The generated overlap information can be used for any genome assembler designed to use such overlapping information to re-construct genome sequences from DNA fragment reads.

The same SHIMMER index can also be utilized to identify the origins of the DNA fragment reads if a known genome is provided. In such case, the DNA reference sequences from a known genome are treated as a special sequence. For any part of the DNA reference sequences, we construct the keys for the HashMap using the neighboring minimizers along different regions of the reference sequences. Then we use the keys to find the HashMap values which are the list of reads that are likely to overlap with the regions of the corresponded keys.

For example, in some embodiments all reads are scanned to construct a hashmap that records the read locations of neighboring minimizer pairs (NMPs), which act as indices in the hashmap. If N is the total number of reads, C is the sequencing coverage, and L is the average read length, then then number of operations to build the hashmap is proportional to the total number bases, approximately GC=NL, where G is the genome size. The number of hashmap indices is therefore proportional to the genome size G. For each unique hashmap index across the entire genome, the number of reads associated with this index is proportional to the sequencing coverage C. Thus, the runtime complexity to construct a SHIMMER index is O(GC) or O(NL).

Assuming roughly uniform distribution across indices (e.g., applicable to non-repetitive sequence regions), the computational cost to determine overlaps scales quadratically with coverage, C. This is due to an all-to-all comparison within each subset of reads that shares an index; that is, for the same neighboring minimizer pair. The number of minimizer indexes in the index is G/d, where d is the average distance between the minimizers, about 500 (see FIG. 4). The overall runtime complexity for the comparison step of some embodiments is thus, $O(GC^2/d)$, which compares favorably with standard overlap-layout-consensus (OLC) approaches, whose algorithmic runtime complexity is quadratic with the number of reads $O(N^2)$ or $O(G^2C^2/L^2)$ because each read must be compared against all others to check the overlapping condition. The ratio of complexity estimates from standard OLC to SHIMMER, $Gd/L^2$, is roughly 5000× for current reads on a human-size genome, where $G\sim10^9$, $d\sim500$, and $L\sim10^4$. It is contemplated if L increases substantially, indexing parameters of the inventive subject matter increase d for improved results. It is further contemplated the inventive subject matter provides dramatic runtime improvements as well.

Figure 1B:
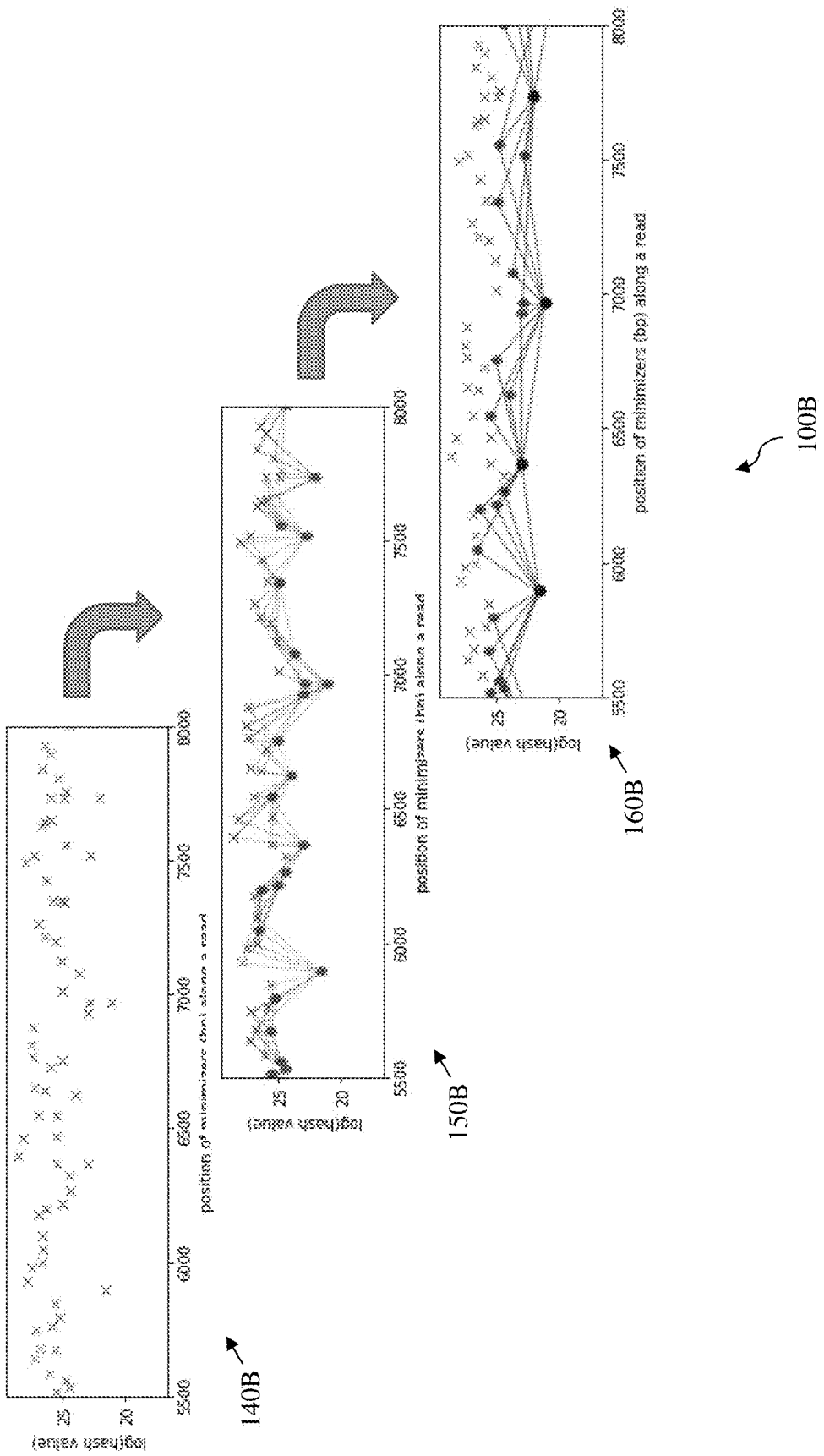
FIG. 1B depicts a pictorial of building an index of the inventive subject matter.

In part, the inventive subject matter extends the concept of database indexing from a list of minimizers to a hierarchy of lists of minimizers. Given a list of lower level minimizers, a hierarchical subset of minimizers is identified to further reduce the index size, as illustrated in diagrams 100A and 100B of FIGS. 1A-B.

In detail, level-0 minimizers 140 (140B) are the k-mers which have lowest hash values 130 over the moving windows 120 along read sequence 110. The hash function is usually chosen to avoid picking minimizers from simple context, e.g. homopolymer stretches. The details of the hash function are typically not important, other than avoiding collisions over the set of k-mers. After generating level-0 minimizers 140 (140B), the list of level-0 minimizers is scanned to identify the subset of minimizers which themselves have the lowest hash values in the level-0 list over moving windows of a given size, for example at least 40. We call this new subset of minimizer "level-1" minimizers (150 and 150B) and the size of the window as reduction factor "r". Similarly, we can repeat the same process over the level-1 minimizers to create level-2 minimizers 160 (160B) and so on, forming a hierarchical structure of minimizers.

Figure 1C:
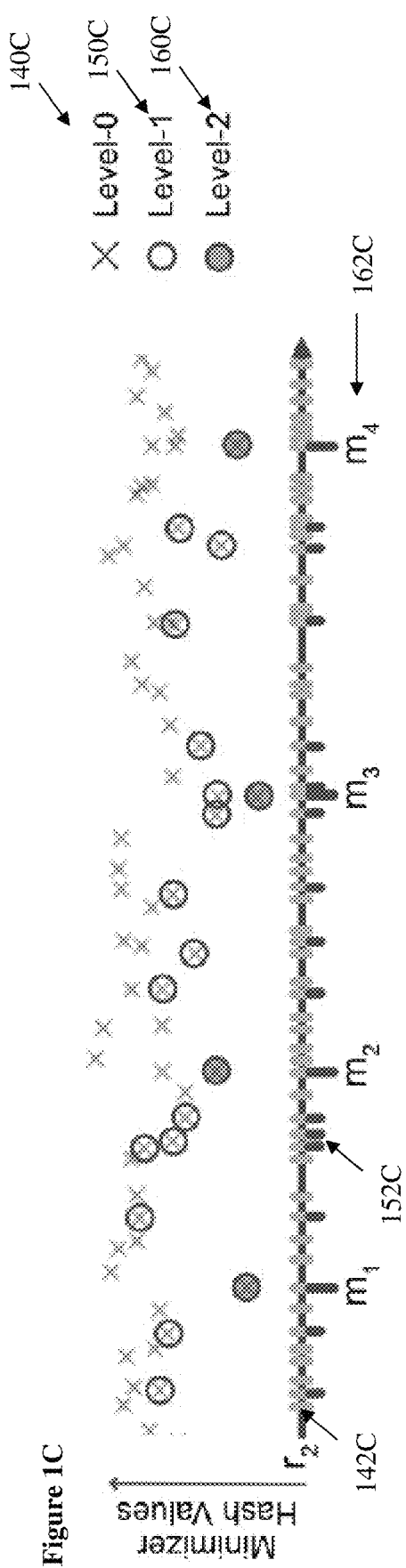
FIG. 1C depicts a further pictorial of an index hashmap of the inventive subject matter.

FIG. 1C depicts hashmap 100C using systems and methods of the inventive subject matter. Gray tick-marks 142C represent the locations of the level-0 minimizer 140C along read $r_2$. The crosses represent the hash value of minimizers 140C. Level-1 minimizers 150C (red tick-marks 152C and circles) are the local minima of the windows through the neighboring minimizers. Similarly, the level-2 minimizers 160C (blue tick-marks 162C ($m_1$ to $m_4$), and filled circles) are local minima of the level-1 minimizers 150C over moving windows.

Figure 1D:
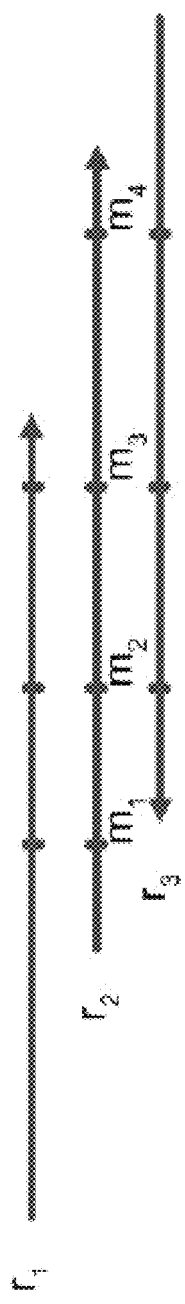
FIG. 1D depicts a pictorial of aligning reads with an index of the inventive subject matter.

FIG. 1D depicts aligning overlapping reads using level-2 minimizers. For each read, the level-2 minimizers are scanned to generate a hashmap that maps neighboring minimizer pairs ($m_1$ to $m_4$) to a set of reads ($r_1$ to $r_3$) to improve overlap finding.

FIG. 2 depicts an example 200 of the process generating different level of minimizers over a simulated read with 1% error from E. coli. We retain the original hash values and the positions of the minimizers in the reads in the different level of indices. In the simulated E. coli dataset, the index size of level-2 minimizers is just 10% (4.98 Mbyte) of the level-0 minimizer index (49.9 M byte) for window size w=80, kmer size k=16 and reduction factor r=6 between the level. The panel 210 of FIG. 2 shows the multiple level minimizers across a read. The black crosses are the level 0 minimizers computed with k=16 and w=80. The red diamonds and the blue dots are the level-1 and level-2 minimizer respectively. The panels 212, 214, and 216 of FIG. 2 shows the steps for building higher level SHIMMER indices. The panel 212 shows the level-0 minimizer in the given window, while panel 214 shows the level 1 minimizers (red diamonds) are the minimizers from those level 0 minimizers. The red lines connect the level 1 minimizers to those level 0 minimizers that the level 1 minimizers are derived from. Panel 216 shows the level 2 minimizers (blue dots), which are generated by finding further minimizers from the level 1 minimizers.

Figure 3:
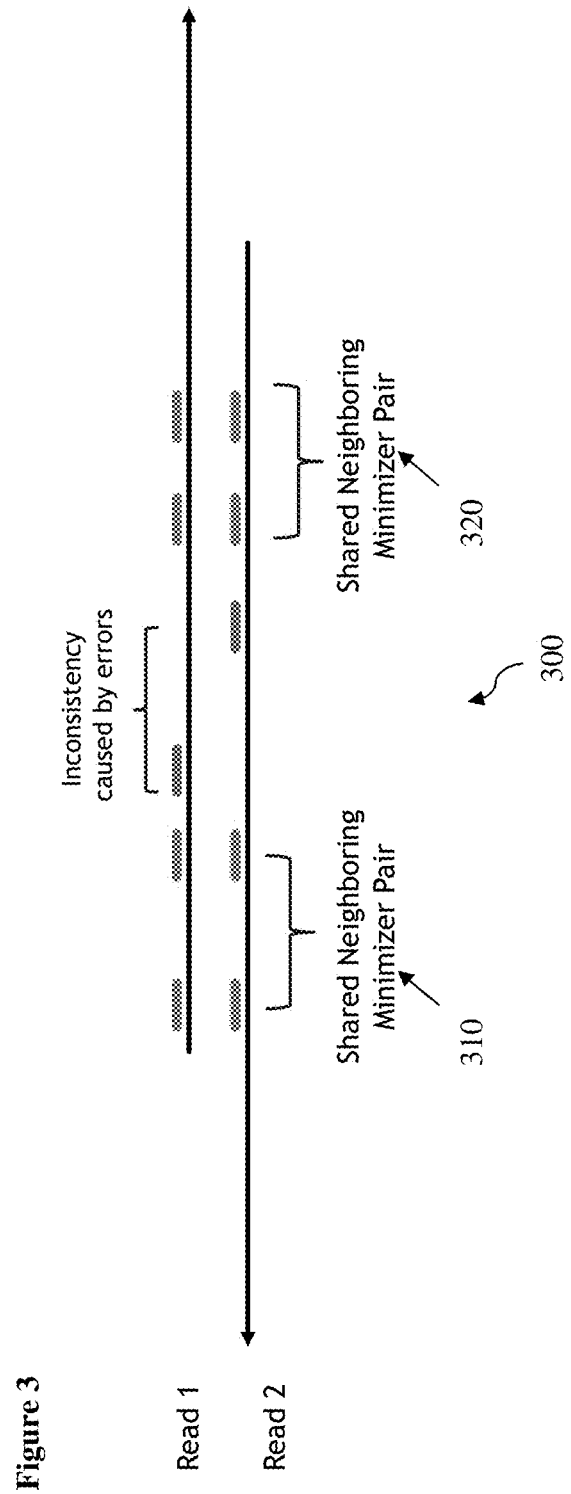
FIG. 3 depicts a pictorial of mapping neighboring minimizer pairs ("NMP") to reads with methods of the inventive subject matter.

The inventive subject matter builds a hashmap (e.g., 300) using NMP (e.g., NMP 310 and 320) as the key from the last level of minimizer list of each read (e.g., read 1 and 2) (FIG. 3, e.g. hashmap F: (Minimizer Pair)→[Read1, Read2, . . . ] for all reads with the same neighboring pairs). The value of the hashmap of a NMP is the list of read identifiers where the NMP can be identified in those reads. Each NMP can be considered as a digest that represents the sequence context across their span. For example, the distance between two neighboring level-0 minimizer pairs is 47.3+/−1.8 bp with w=80 and k=16 in the *E. coli* dataset. In such case, two sequences of 47 bps with that same NMP are likely identical to each other.

Figure 4:
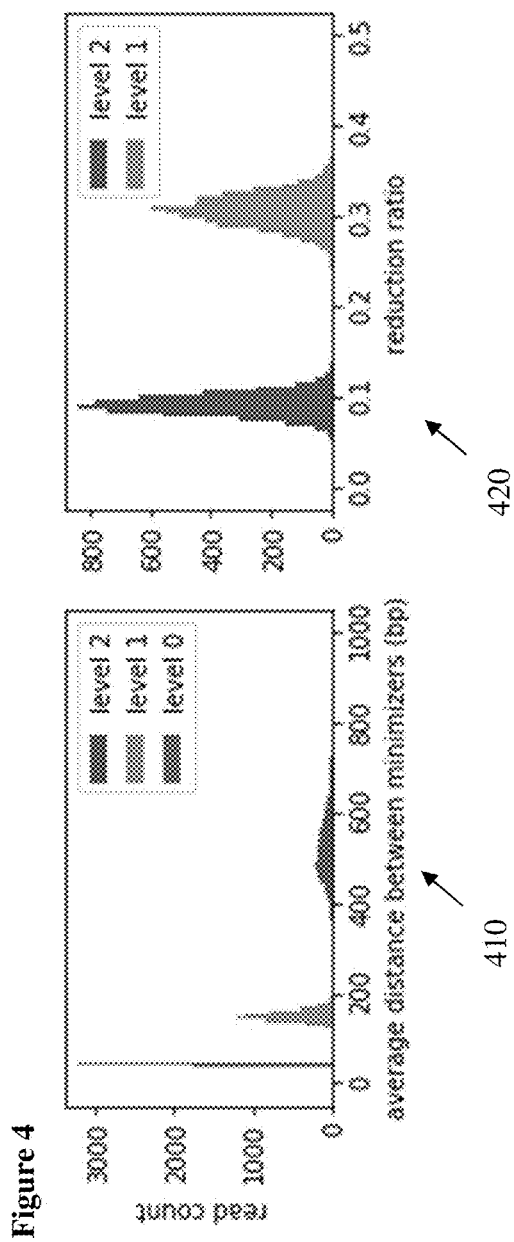
FIG. 4 depicts graphs of read counts for NMPs with methods of the inventive subject matter.

The NMP from higher level minimizers spans larger and larger range across the reads. For example, the distance between two neighboring level-2 minimizers is 527.9+/−74.6 bp after two levels of reduction of the minimizer with a reduction factor r=6 (FIG. 4). It is about 7.1 times longer than the neighboring distance between the depicted level-0 minimizers. Pane 410 of FIG. 4 shows the distribution of the average distance between minimizers of different levels, while pane 420 shows the distribution of the reduction ratio, calculated as (number of level 1 or 2 minimizers)/(number of level 0 minimizers) per read. FIGS. 1A-D and FIG. 5 depict the overview of building and using a SHIMMER index of the inventive subject matter. For example, flow chart 500 illustrates step 510, 520, 530, and 540 to assemble contigs.

Figure 6A:
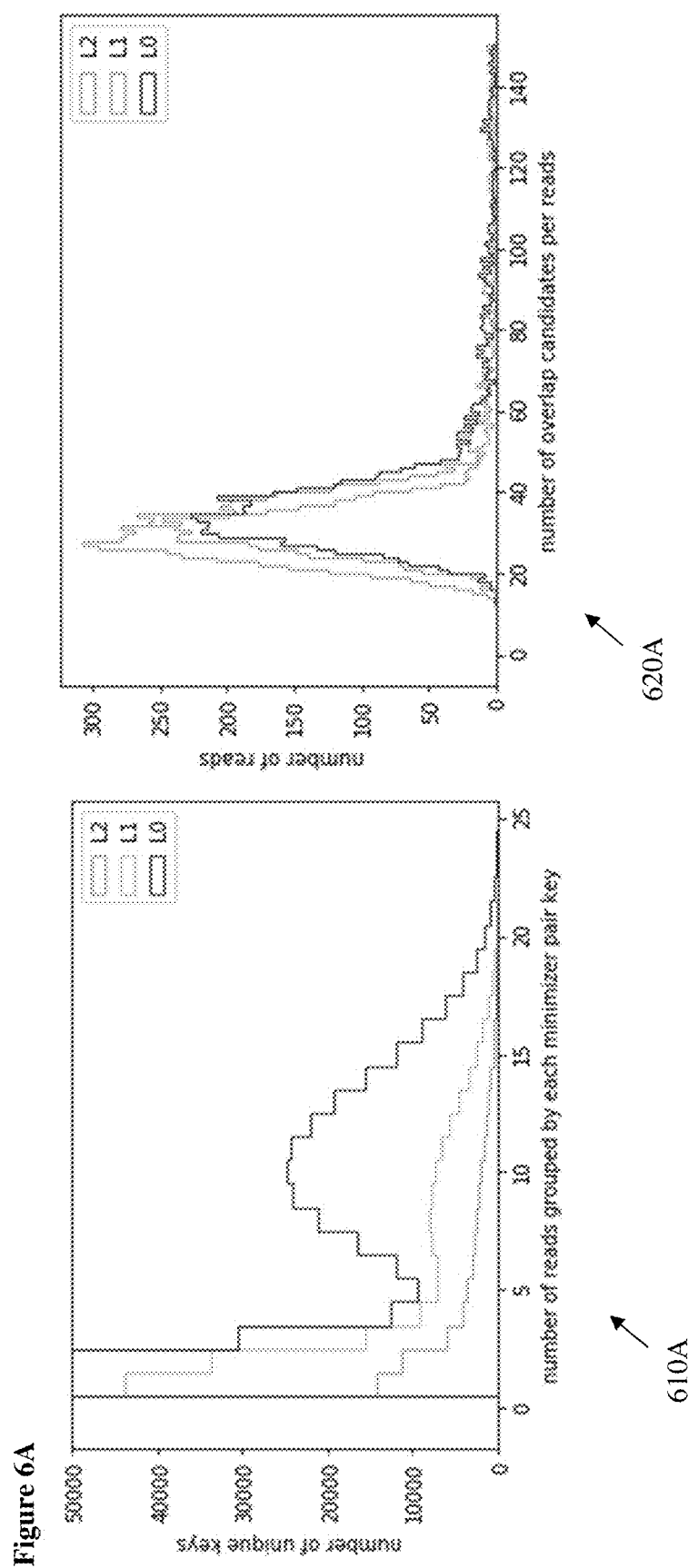
FIGS. 6A and 6B depicts graphs of the read counts for NMPs of the inventive subject matter.
Figure 6B:
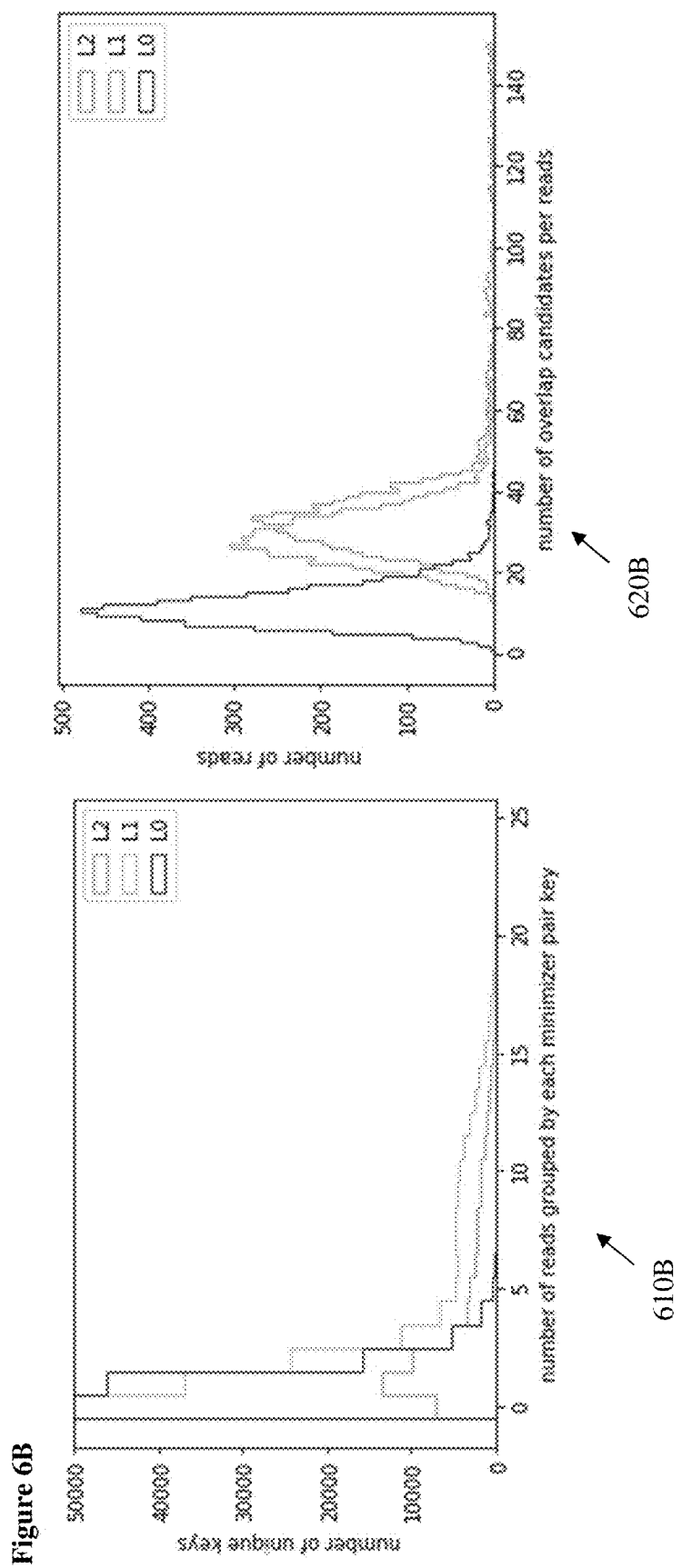

FIGS. 6A-B show the number of unique NMP keys and the number of reads that are gathered by each NMP. To avoid indexing NMP with two minimizers that are too close to each other, a minimum distance requirement is used. For example, a minimum distance between minimizers can be set to exclude minimizers that are less than 100 bp apart. As distances between level-1 or level-2 minimizers increases, the minimum distance filter has little effect on overall overlapping performance, but avoids indexing high density NMPs in repetitive regions of the genetic sequence.

FIG. 6A demonstrates the minimizers are close to each other when distance between NMPs is not filtered. Pane 610A shows the distribution of number of hits per unique NMP, while pane 620A shows the distribution of the number reads that can be identified as overlapped reads using all MNPs in a read. The average number of hits per NMP key for level-0 is 483869 unique NMPs, with 6.15 hits/per key. For level-1, the average number of hits per NMP key is 174744 unique NMPs with 5.19 hits/per NMP. For level-2, the average number of hits per NMP key is 57842 unique NMPs with 4.68 hits/per NMP. The average number of read overlaps for level-0 is 51.3, for level-1 is 44.8, and for level-2 is 32.5.

FIG. 6B shows filtering to remove NMPs with minimizers less than 100 bp apart. Pane 610B shows the distribution of number of hits per unique NMP, while Pane 620B shows the distribution of the number reads that can be identified as overlapped reads using all NMPs in a read. The average number of hits per NMP key for level-0 is 483869 unique NMPs with 0.218 hits/per key. For level-1, the average number of hits per NMP key is 174744 unique NMPs with 3.24 hits/per NMP. For level-2, the average number of hits per NMP key is 57842 unique NMPs with 3.95 hits/per NMP. The average number of read overlaps for level-0 is 11.67, for level-1 is 42.8, and for level-2 is 31.9.

The reads that are grouped by each NMP have a high probability of coming from the same region of the genomic sequence. A detail alignment between the reads of each group confirms the overlap. (Myers, Eugene W. "AnO (ND) difference algorithm and its variations." Algorithmica 1, no. 1-4 (1986): 251-266.) As only the reads need to be compared within each group, global genome read-to-read comparison is avoided. As multiple NMPs may identify the same read pairs for overlapping, reads can be recorded that are tested for overlapping to avoid duplicated computations.

For eukaryotic genomes, it is beneficial to identify sequence repeats in the early stages of genome assembly to avoid unnecessary and burdensome computation. In highly repetitive genome regions $C^2$ scaling breaks down because a single NMP may correspond to many loci in the genome. The NMPs that likely correspond to long repetitive sequences are preferably identified in the indexing process; the number of corresponding reads is statistically greater from reads expected for uniform coverage. In some embodiments, high repeat NMPs are preferably ignored and incorporated into genome assembly is separate, downstream analysis without compromising the runtime complexity.

Figure 8:
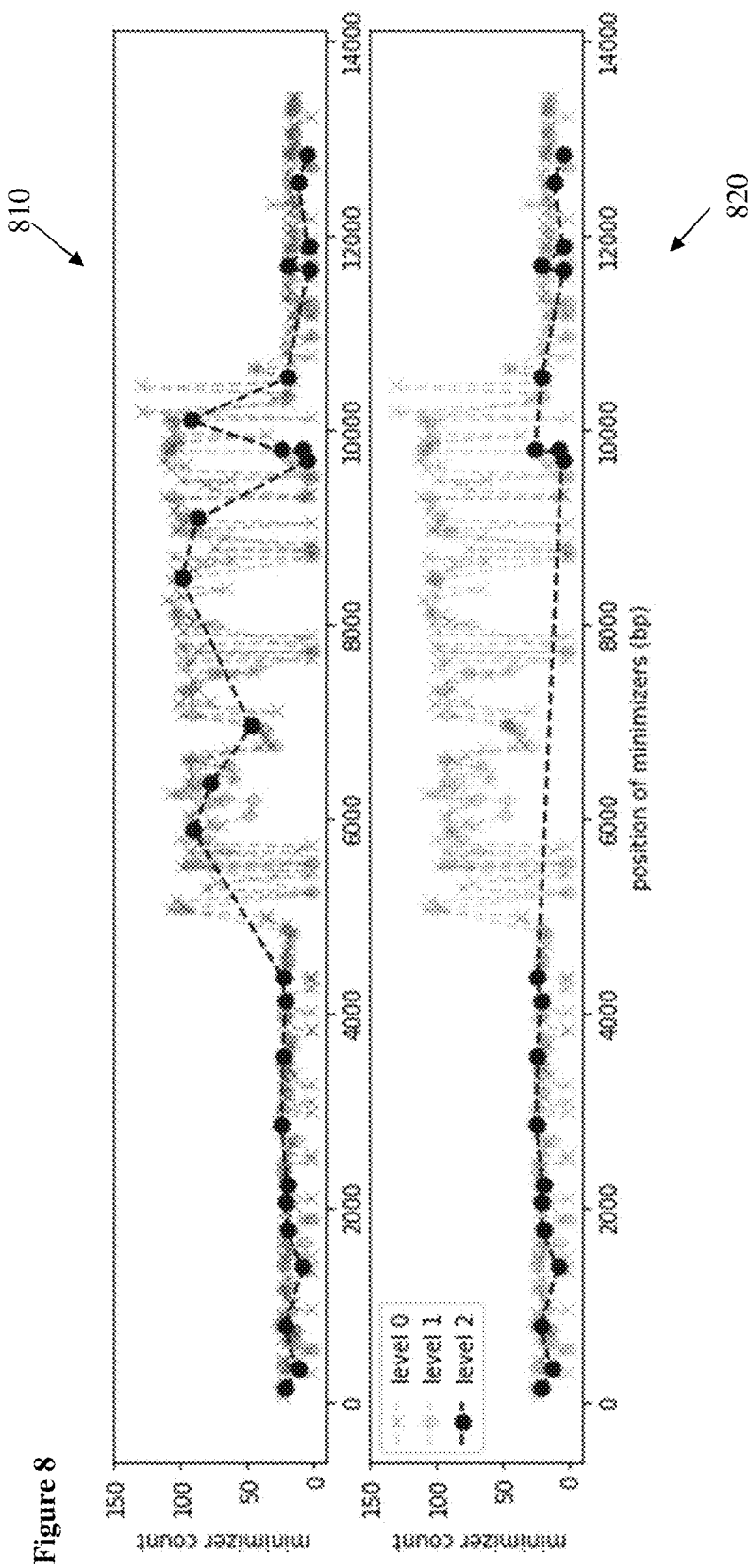
FIG. 8 depicts two hashmaps using methods of the inventive subject matter.

Viewed from another perspective, if an NMP is mapped to too many reads, the sequence that the NMP represents is likely from a repetitive sequence in the genome and can be excluded from the initial genome assembly and later included in final assembly. FIG. 8 shows an example of filtering out high repeat count minimizers in a read. The minimizer count shows there is a repetitive segment from about 5,000 bp to 11,000 bp in this read. If we filter out minimizers with excessive count, e.g. greater than 50 in this example, we can reduce false hits caused by such repeats. We can still use the minimizers for the unique part to find proper overlaps. Pane 810 has blue dots showing the level-2 minimizers before high repeat count filtering, while pane 820 has blue dots showing the level-2 minimizers after filtering.

The SHIMMER indexing schema is also useful for mapping fast reads to contig, or contig to reference mapping. For the consensus step, we map the reads 710 back to the contig 720 (e.g., portion 722 depicted) using the SHIMMER indices (NMPs 730) from the contigs and the reads, as depicted in diagram 700 of FIG. 7. Once the reads are mapped to each contig, further analysis, for example the FALCON-sense DAG consensus module (Berlin, Konstantin, Sergey Koren, Chen-Shan Chin, James P. Drake, Jane M. Landolin, and Adam M. Phillippy. "Assembling large genomes with single-molecule sequencing and locality-sensitive hashing." Nature biotechnology 33, no. 6 (2015): 623.), is applied to generate the final consensus and improve the contig accuracy.

For example, the final consensus base accuracy is affected by multiple factors, such as (1) input quality in terms of read length, accuracy and overall sequencing coverage, (2) repeat content, and (3) heterozygosity. For simulated *E. coli* reads, embodiments of the inventive subject matter achieve 100% accuracy after consensus. Real world sequencing data (especially for eukaryotes) present additional challenges. For example, systems and methods of the inventive subject matter typically select an allele with majority read support on the heterozygous SNP sites, and may fail to pick the correct allele if there are complicated multiple local variants between two haplotypes. In some embodiments diploid or polyploid genomes are considered in steps following the SHIMMER indexing and overlapping steps. For example, techniques developed by earlier work (e.g. FALCON-Unzip 25 or Canu Trio binning 29) can be adapted to downstream or upstream processing to obtain pseudo-haplotigs or haplotigs.

Figure 5:
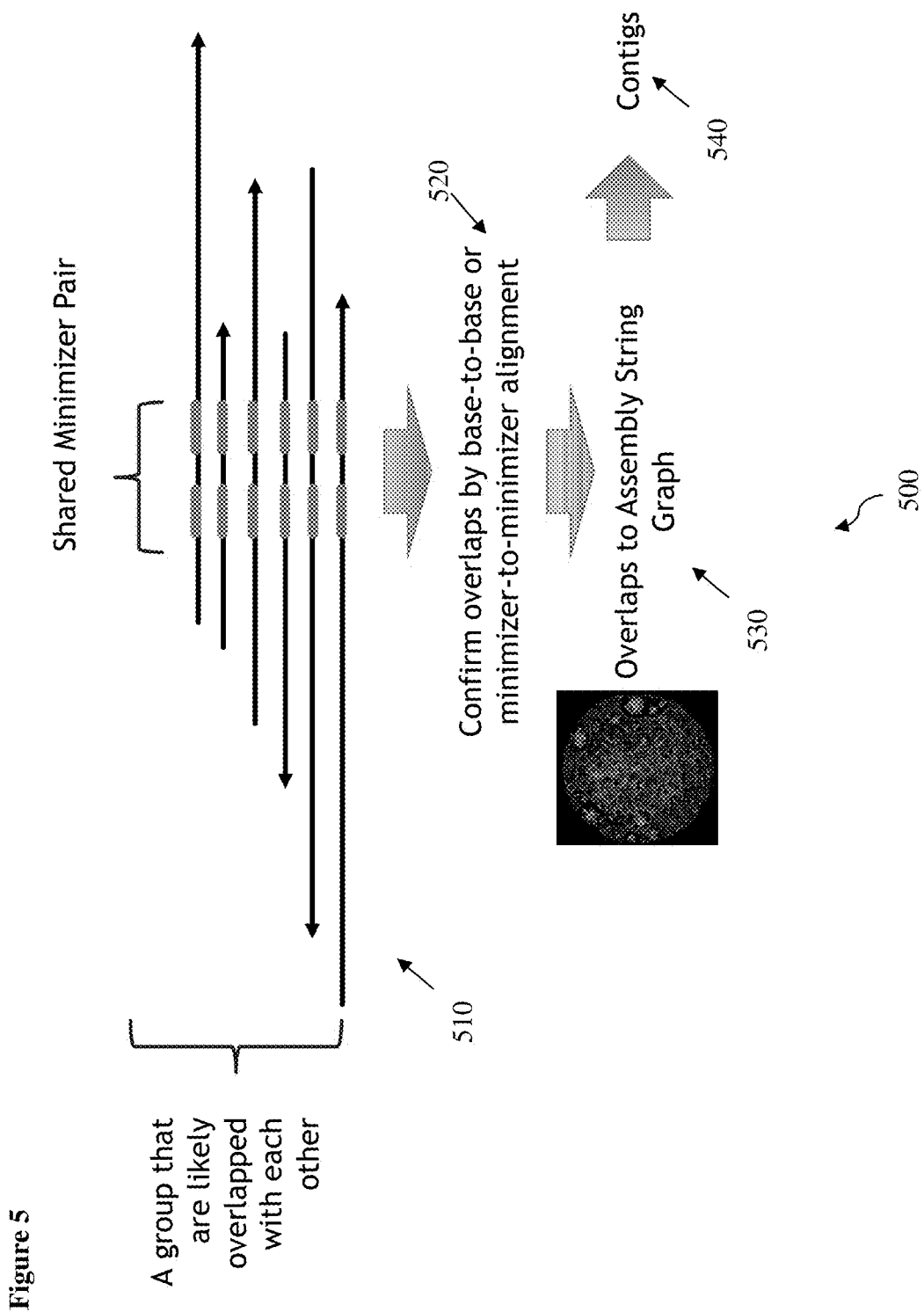
FIG. 5 depicts a pictorial workflow of methods of the inventive subject matter.

The inventive subject matter can be used to implement a new genome assembler, here termed "Peregrine" (FIG. 5). FIGS. 9-12 depict data from using the Peregrine assembler of the inventive subject matter on human genome datasets with different parameter sets utilizing large memory instances (e.g. m5d.metal or r5d.12xlarge) from AWS to run 24 indexing and overlapping processes concurrently. In this embodiment, Peregrine uses 9 to 25 CPU core hours depending the sequencing coverage and parameters. The wall clock time of a typical assembly run ranges from one to two hours from initial DNA read files. It is also possible to run the indexing and overlapping steps with a smaller memory footprint as embodiments of Peregrine's indexing and overlapping modules are flexible, for example using different numbers of partitions, each process can be run in serial on smaller partitions to reduce the memory requirement, etc. For example, some Peregrine embodiments can assemble 30× human PacBio CCS read datasets in less than 30 CPU hours and around 100 wall-clock minutes to a high contiguity assembly (N50>20 Mb).

FIG. 12 depicts data from a Benchmarking Universal Single-Copy Orthologs (BUSCO) evaluation with the vertebrata lineage profile on the selected assemblies of three different human genomes. The BUSCO completeness ranges from 94% to 95.2%. For this BUSCO evaluation, the results of the inventive subject matter are on-par or higher than most de novo human genome assemblies from similar data. The CPU core hour usage of systems and methods of the inventive subject matter is significantly lower than assemblers known in the art applied to the same HG002 dataset and achieve the same or slightly better BUSCO performance. For assembly contiguity, systems and methods of the inventive subject matter perform on-par or better than assemblers known in the art.

In some embodiments, adjustments are made to accommodate reduced accuracy of the reads (e.g., more than 1%, 3%, 5%, 10% error rate, etc.) by modifying the indexing parameters and incorporating additional denoising steps to the process. Likewise, the inventive subject matter can be favorably applied to improvements in sequencing technology, such as read lengths increasing beyond the current technology limit of ~15 kb.

It should be appreciated that the inventive subject matter provides significant improvement to computer performance in genome sequencing, enabling computer hardware to perform functions previously unattainable. For example, compute processes for data assembly, specifically whole genome sequencing, are greatly accelerated. Indeed, systems and methods of the inventive subject matter enable users to construct partial or complete genome models previously unattainable with restricted logistical, financial, or hardware resources. Further, the inventive subject matter provides significant reduction in computer resource consumption. For example, the inventive subject matter enables human genome assembly in about two hours with cloud-accessible hardware on a single node. Similarly, a dedicated desktop computer with sufficient physical memory (e.g. 2019 Mac Pro) can also perform this task without the need for a cluster computer setup, which avoids both software infrastructure requirements and the need for specialized skills in grid computing.

Moreover, the inventive subject matter enables unprecedented access of patients to healthcare specifically targeted to the patient's specific genome, as well as ongoing improvements or tuning of therapies based on changes in the patient's genome. The inventive subject matter enables routine generation of human de novo assemblies, allowing for population scale measurements of more comprehensive genomic variations—beyond SNPs and small indels—as well as novel applications requiring rapid access to de novo assemblies.

In some embodiments, the k-mer size used for constructing the SHIMMER index can be such as 8, 9, 10, 11, 12, 13, 14, 15, 16, 17, 18, 19, 20, 21, 22, 23, 24, 32, 48, 56, 64, 128, 256. In some embodiments, the window size w used for constructing the SHIMMER index can be such as 24, 28, 32, 36, 40, 48, 56, 64, 72, 84, 96, 128, 256, 512, 1024, 2048, 4096, 8192, and 16384. In some embodiments, the reduction factor r used for constructing the SHIMMER index can be such as 1, 2, 3, 4, 5, 6, 7, 8, 9, 10, 11, 12, 16, 20, 24, 28, 32, 40, 48, 56, 64, 72, 96, 128, 256, and 512. In some embodiments, the number of levels used for constructing the SHIMMER index can be such as 0, 1, 2, 3, 4, 5, 6, 7, 8, 9, 10, 11, and 12. In some embodiments, the distance used for filtering neighboring minimizers can be such as 10, 20, 30, 40, 50, 60, 70, 80, 90, 100, 150, 200, 250, 300, 400, 500, 600, 700, 800, 900, 1000, 2000, 3000, 4000, 5000, and 10000. In some embodiments, the average input DNA read lengths can be such as 1000, 2000, 3000, 4000, 5000, 6000, 7000, 8000, 9000, 10000, 11000, 12000, 13000, 14000, 15000, 16000, 17000, 18000, 19000, 20000, 25000, 30000, 40000, 50000, 100000, 200000, 300000, 400000, 500000, and 1000000. In some embodiments, the error rates of the input DNA reads can be such as 0%, 0.001%, 0.01%, 0.05%, 0.1%, 0.5%, 1%, 2%, 3% 4%, 5%, 10%, 15% and 20%. In some embodiments, the number of minimizers used inside NMP can be such as 2, 3, 4, 5, 6, 7, 8, 9, 10, 11, 12.

In preferred embodiments, the methods provided herein are computer-implemented methods, wherein at least one or more steps of the method are carried out by a processor executing instructions encoded in a computer program. In some embodiments, the methods provided herein are implemented in a computer program stored on computer-readable media, such as the hard drive of a computer, or portable storage media. For example, a computer program for determining a SHIMMER index can include one or more of the following: code for building database from sequence reads, code for generating minimizers, code for constructing the HashMap mapping the neighboring minimizers to the reads, code for confirming overlapping between a pair of reads, code for generating the overlap information output.

Furthermore, the functional aspects of the invention that are implemented on a computer or other logic processing systems or circuits, as will be understood to one of skill in the art, may be implemented or accomplished using any appropriate implementation environment or programming language, such as C, C++, Python, Rust, Cobol, Pascal, Java, Java-Script, HTML, XML, dHTML, assembly or machine code programming, RTL, etc.

In certain embodiments, various steps of the method utilize information and/or programs, and generate results that are stored on computer-readable media, e.g., a hard drive, auxiliary memory, external memory, server, database, or a portable memory device such as a CD-R, DVD, ZIP disk, flash memory card. For example, information used for and results generated by the methods that can be stored on computer-readable media include but are not limited to sequence information (e.g., sequence reads), the generated minimizers, the generated HashMap from neighboring minimizers to sequence reads, the generated groups of reads that shared the same neighboring minimizers, and the generated overlapped read information.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method to reduce memory storage, reduce compute time, and improve performance of a computer system for assembling an unknown genetic sequence from a plurality of at least partially duplicate segments of the genetic sequence, comprising:

applying the computer system to identify at least two segments with a first level of common neighboring base pairs and organizing them in a plurality of first level groups;

applying the computer system to only assemble each of the first level groups into a contiguous sequence of base pairs; and applying the computer system to only assemble each of the contiguous sequences into the genetic sequence.

2. The method of claim 1, wherein the segments are more than ten base pairs long.

3. The method of claim 1, wherein the first level of common neighboring base pairs are identified in a read window of at least forty base pairs.

4. The method of claim 1, wherein the first level of common neighboring base pairs are separated by at least fifty base pairs.

5. The method of claim 1, further comprising:

applying the computer system to further identify groups from the first level groups with a second level of common neighboring base pairs and organize them in a plurality of second level groups;

applying the computer system to further assemble only each of the second level groups into a contiguous sequence of base pairs; and applying the computer system to further assemble only each of the contiguous sequences into the genetic sequence.

6. The method of claim 5, wherein the second level of common neighboring base pairs are separated by at least three hundred base pairs.

7. The method of claim 5, further comprising:

applying the computer system to further identify groups from the second level groups with a third level of common neighboring base pairs and organize them in a plurality of third level groups;

applying the computer system to further assemble only each of the third level groups into a contiguous sequence of base pairs; and applying the computer system to further assemble only each of the contiguous sequence of base pairs into the genetic sequence.

8. A method to reduce memory storage, reduce compute time, and improve performance of computer system for structuring a plurality of at least partially duplicate segments of a genetic sequence, comprising:

applying the computer system to only assemble a plurality of primary groups, wherein each primary group comprises segments with a first order of common neighboring base pairs; and applying the computer system to further assembles only the plurality of primary groups into a plurality of secondary groups, wherein each primary group in a secondary group includes a segment with a second order of common neighboring base pairs.

9. The method of claim 8, wherein the segments are more than ten base pairs long.

10. The method of claim 8, wherein the first order of common neighboring base pairs are separated by at least fifty base pairs.

11. The method of claim 8, wherein the second order of common neighboring base pairs are separated by at least three hundred base pairs.

12. The method of claim 8, further comprising applying the computer system to further assemble only the plurality of secondary groups into a plurality of tertiary groups, wherein each secondary group in a tertiary group includes a segment with a third order of common neighboring base pairs.

13. The method of claim 8, wherein the first order of common neighboring base pairs are identified in a read window of at least eighty base pairs.

14. The method of claim 12, wherein the third order of common neighboring base pairs are separated by at least six hundred base pairs.

15. A method to reduce memory storage, reduce compute time, and improve performance of a computer system for assembling a data sequence from a plurality of at least partially duplicate segments of the data sequence:

applying the computer system to identify segments with a first level of common neighboring data elements and organize them in a plurality of first level groups;

applying the computer system to identifying groups from only the first level groups with a second level common neighboring data elements and organize them in a plurality of second level groups;

applying the computer system to assemble only each of the second level groups into a contiguous sequence of data elements; and applying the computer system to assemble each of the contiguous sequence of data elements into the data sequence.

16. The method of claim 15, wherein the sequences are more than ten data elements long.

17. The method of claim 15, wherein the first level of common neighboring data elements are identified in a read window of at least forty data elements.

18. The method of claim 15, wherein the first level of common neighboring data elements are separated by at least fifty data elements.

19. The method of claim 15, wherein the second level of common neighboring data elements are separated by at least five hundred data elements.

* * * * *